United States Patent
Yamamori et al.

(10) Patent No.: US 6,191,421 B1
(45) Date of Patent: *Feb. 20, 2001

(54) GAS ANALYZER USING INFRARED RADIATION TO DETERMINE THE CONCENTRATION OF A TARGET GAS IN A GASEOUS MIXTURE

(75) Inventors: Shinji Yamamori; Hidetoshi Dainobu; Hidehiro Hosaka, all of Tokyo (JP)

(73) Assignee: Nihon Kohden Corporation, Tokyo (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/943,235

(22) Filed: Oct. 3, 1997

(30) Foreign Application Priority Data

Oct. 3, 1996 (JP) .................................. 8-2629523

(51) Int. Cl.$^7$ ......................... G01N 21/61; G01N 21/35
(52) U.S. Cl. ................ 250/343; 250/345; 250/339.01; 422/84; 356/436
(58) Field of Search ........................... 250/343, 345, 250/339.01; 422/84; 356/436

(56) References Cited

U.S. PATENT DOCUMENTS

| | | |
|---|---|---|
| 3,811,776 | 5/1974 | Blau, Jr. . |
| 3,987,303 | 10/1976 | Stoft et al. . |
| 4,075,481 | 2/1978 | Stoft et al. . |
| 4,176,963 * | 12/1979 | Fabinski et al. ................... 356/418 |
| 4,468,561 | 8/1984 | Speeter . |
| 5,092,342 | 3/1992 | Hattendorff et al. . |
| 5,095,900 | 3/1992 | Fertig et al. . |
| 5,146,092 | 9/1992 | Apperson et al. . |
| 5,153,436 | 10/1992 | Apperson et al. . |
| 5,214,593 * | 5/1993 | Magnussen, Jr. et al. .......... 356/436 |
| 5,464,982 | 11/1995 | Drucker et al. . |
| 5,693,945 | 12/1997 | Akiyama et al. . |

FOREIGN PATENT DOCUMENTS

| | | |
|---|---|---|
| 60-205236 | 10/1985 | (JP) . |
| 8-122254 | 5/1996 | (JP) . |
| WO 96/07886 | 3/1996 | (WO) . |

* cited by examiner

Primary Examiner—Constantine Hannaher
Assistant Examiner—Andrew Israel
(74) Attorney, Agent, or Firm—Sughrue, Mion, Zinn, Macpeak & Seas, PLLC

(57) ABSTRACT

A capnometer includes an airway adaptor for introducing a respiratory gas into the analyzer, an infrared radiation source emitting infrared radiation passed through the airway adaptor, a beam splitter for reflecting and transmitting infrared radiation that impinges on the beam splitter, first detecting means for detecting the infrared radiation reflected by said beam splitter and transmitting through said beam splitter, second detecting means for detecting the infrared radiation reflected by said beam splitter and transmitting through said beam splitter; a gas cell filled with $CO_2$ gas, said gas cell being located between one of said first and second detecting means and said beam splitter and processing means for processing a concentration of carbon dioxide gas by using output signals of said first and second detecting means.

6 Claims, 5 Drawing Sheets

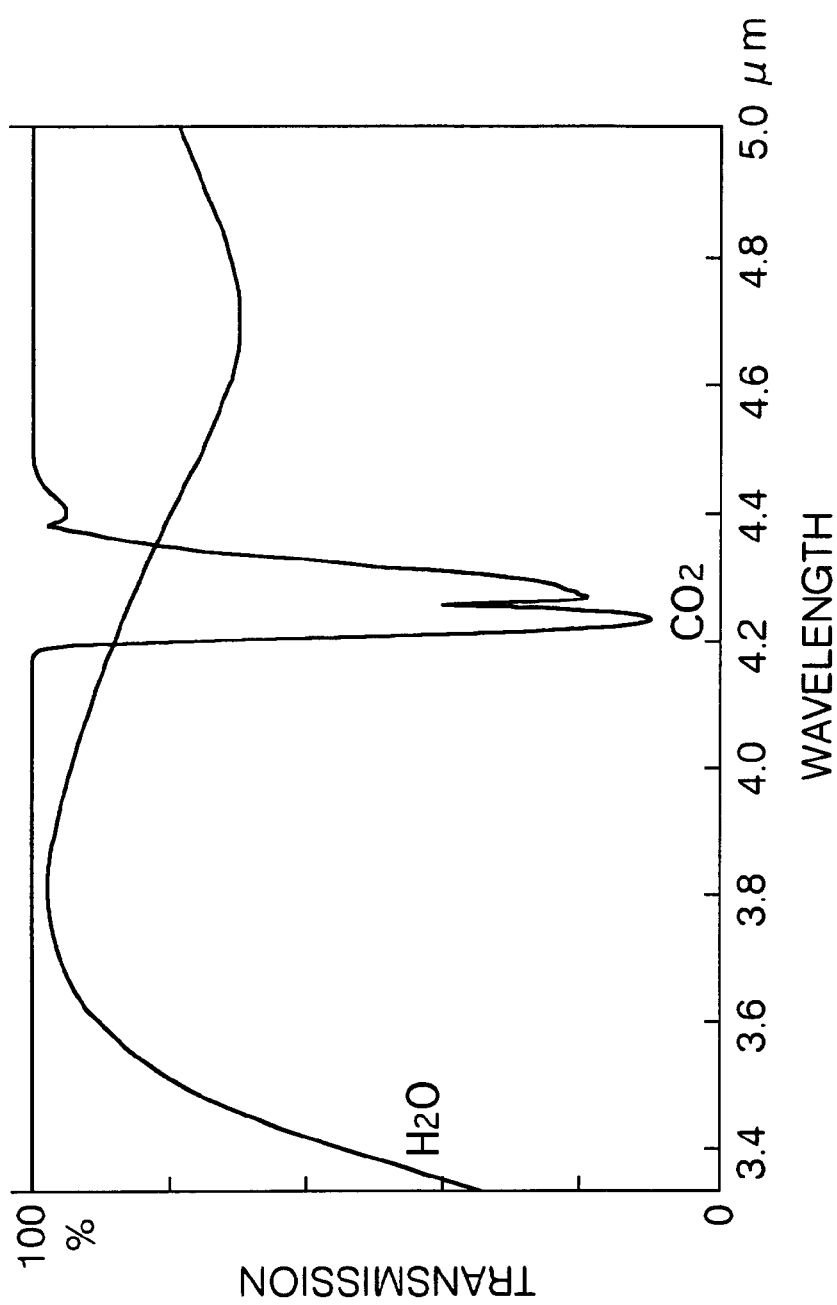

GAS ANALYZER USING INFRARED RADIATION TO DETERMINE THE CONCENTRATION OF A TARGET GAS IN A GASEOUS MIXTURE

BACKGROUND OF THE INVENTION

1. Field of the Invention

The present invention relates to an instrument for measuring a concentration of carbon dioxide contained in a respiratory gas by non-dispersive infrared method.

2. Related art

This type of instrument is called a capnometer. A typical example of the known capnometer is the non-dispersive infrared radiation analyzer. In the capnometer, to measure a concentration of $CO_2$ gas contained in the respiratory gas, infrared radiation is emitted from infrared radiation source, and passed through the respiratory gas. The concentration of $CO_2$ gas can be measured by passing a beam of infrared radiation through the gas, and ascertaining the attenuation of the intensity of infrared radiation in a narrow wavelength band which is remarkably absorbed by $CO_2$ gas. A wavelength of approximately 4.3 $\mu$m is used for this purpose as a measuring wavelength, and a wavelength of approximately 3.7 $\mu$m which is not absorbed by the carbon dioxide is used as a reference wavelength. As known, a relation between the concentration of $CO_2$ gas and an intensity of light is shown by the Lambert-Beer relation, and is given by $$Iout = Iin \exp(-kcl)$$

where

Iin: intensity of light going into the sample.

Iout: intensity of light coming out of the sample.

k, c, l: absorption coefficient, concentration of $CO_2$ gas, and optical length respectively.

The equation shows that a concentration c of $CO_2$ gas can be measured if the Iin, Iout, k and l are known.

The capnometer based on above principle is disclosed in U.S. Pat. No. 5,153,436. A schematic illustration of the analyzer is shown in FIG. 4. In the figure, reference numeral 30 is a housing of a measuring section, and 31 is an airway adaptor used for introducing respiratory gases of a patient into the analyzer. The airway adaptor 31 is inserted directly in the flow path between the ventilator and the endotracheal tube (not shown), which is extended in the directions vertical to the paper surface of the drawing. Windows 32 and 33 are respectively formed in both sides of the airway adaptor 31. These windows are made of sapphire having a good transparency to the infrared radiation. The airway adaptor 31 is firmly held in a receptacle portion 34 of the housing 30 in a detachable fashion. The airway adaptor 31 may be the reusable type or the disposal type.

An infrared radiation source 35 is disposed in the left hand of the receptacle portion 34. A light beam is emitted from the infrared radiation source 35, passes through a sapphire window 34a disposed in proximity to the left hand of the receptacle portion 34, and the windows 32 and 33 of the airway adaptor 31 and a sapphire window 34b disposed in proximity to the right hand of the receptacle portion 34, and reaches a beam splitter 36. The beam splitter 36 may be a dichroic mirror which reflects the infrared radiation having a wavelength longer than about 4 $\mu$m but allows the infrared radiation having a wavelength shorter than about 4 $\mu$m to transmit therethrough. The beam splitter 36 is slanted approximately 45° with respect to the optical axis of the infrared radiation source 35. The infrared radiation is impinging on the beam splitter 36. Infrared radiation having a wavelength longer than 4 $\mu$m is reflected and directed to the lead selenide (PbSe) detector 38 through a bandpass filter 37 which transmits wavelength in the range of about 4.3 $\mu$m. Infrared radiation having a wavelength shorter than 4 $\mu$m is, instead, transmitted through the beam splitter 36 and impinging on the lead selenide detector 40 through a bandpass filter 39 which transmits wavelength in the range of about 3.7 $\mu$m.

Infrared spectrum of carbon dioxide gas is shown in FIG. 5. As seen from the spectrum diagram, the least transmittance of the carbon dioxide gas appears at its wavelengths near to 4.3 $\mu$m, and the transmittance is approximately 100% at 3.7 $\mu$m. In other words, most of infrared radiation having a wavelength of 4.3 $\mu$m is absorbed by the carbon dioxide gas, while infrared radiation having a wavelength of 3.7 $\mu$m is not absorbed. From this fact, it is seen that a concentration of the $CO_2$ gas can be obtained by calculating a ratio of electrical signals, which are derived from the two detectors 38 and 40, propotional to the intensity of the infrared radiation impinging on them.

A heater h and a thermistor s are attached to a portion (of the receptacle portion 34) of the housing 30 where the housing comes in contact with the airway adaptor 31. The thermistor s senses temperature of the heater h. The heater h heats the airway adaptor 31 in order to avoid the condensation of water vapor on the inner surfaces of the windows 32 and 33 by highly humidified respiratory gases.

In the conventional art, as seen from the foregoing description, where the inner surfaces of the windows 32 and 33 are soiled with secretion, e.g., sputum, whose absorption amounts of the infrared radiation at 4.3 $\mu$m and 3.7 $\mu$m are different from each other, the absorption amount difference causes a false calculation of the carbon dioxide concentration.

In the conventional art, a heat source, a lamp, or the like is used for the infrared radiation source. If such an infrared radiation source suffers from degradation, drift or the like, its temperature varies. As a result, not only the intensity of the emitted light varies at 4.3 $\mu$m and 3.7 $\mu$m, but also the ratio of the intensity of the infrared radiation impinging on the two detectors 38 and 40 varies as shown by Planck's law of radiation.

As described above, the prior airway adaptor is high in cost to manufacture because expensive sapphire is used for the windows of the airway adaptor.

To avoid the codensation of water on surfaces of the windows of the airway adaptor, the airway adaptor is heated by the heater. The use of the heater causes an increase of power consumption, requires a long warm-up time. In other words, a quick measurement of the $CO_2$ gas concentration from cold start is impossible in the prior analyzer.

The infrared radiation of two wavelengths, 4.3 $\mu$m and 3.7 $\mu$m, are used for measuring the carbon dioxide gas concentration. Therefore, the $CO_2$ gas concentration measurement may be inaccuate by the soils of the windows of the airway adaptor, the degradation and drift of the infrared radiation source, and is instable.

SUMMARY OF THE INVENTION

Accordingly, an object of the present invention is to provide a capnometer which is free from the adverse influence by soils of windows, and the degradation and drift of the infrared radiation source, and further consumes less electric power.

According to an aspect of the present invention, there is provided a capnometer comprising: an airway adaptor for introducing a respiratory gas into the analyzer; an infrared radiation source emitting infrared radiation passed through the airway adaptor; a beam splitter for reflecting the infrared radiation impinging thereon and allowing the infrared radiation to transmit therethrough; first detecting means for detecting the infrared radiation reflected by said beam splitter or transmitting through said beam splitter; second detecting means for detecting the infrared radiation reflected by said beam splitter or transmitting through said beam splitter; a gas cell filled with $CO_2$ gas, said gas cell being located between one of said first and second detecting means and said beam splitter; and processing means for processing a concentration of $CO_2$ gas by using output signals of said first and second detecting means.

As seen from the foregoing description, in the capnometer of the present invention, the detectors detect the each infrared radiation having an equal wavelength. Therefore, the analyzer can exactly measure the concentration of carbon dioxide independently of soils of the windows, and the degradation and drift of the infrared radiation source.

In the embodiment of the invention, there is no need for the heater and thermistor, which are indispensable for preventing the windows of the airway adaptor from being fogged in the conventional capnometer. This feature contributes to reduction of power consumption by the analyzer and simplification of the analyzer construction.

Further, there is no need for expensive material, such as sapphire, for the windows of the airway adaptor. Besides, such a simple and inexpensive beam splitter as to be able to reflect the infrared radiation and allow the same to transmit therethrough is available for the capnometer of the embodiment of the invention, while an expensive dichroic mirror capable of splitting two infrared radiation of different wavelengths is used for the conventional analyzer.

BRIEF DESCRIPTION OF THE DRAWINGS

FIG. 5 is an infared transmittance spectrum diagram of $CO_2$ gas and water.

DETAILED DESCRIPTION OF THE PREFERRED EMBODIMENTS

Figure 1:
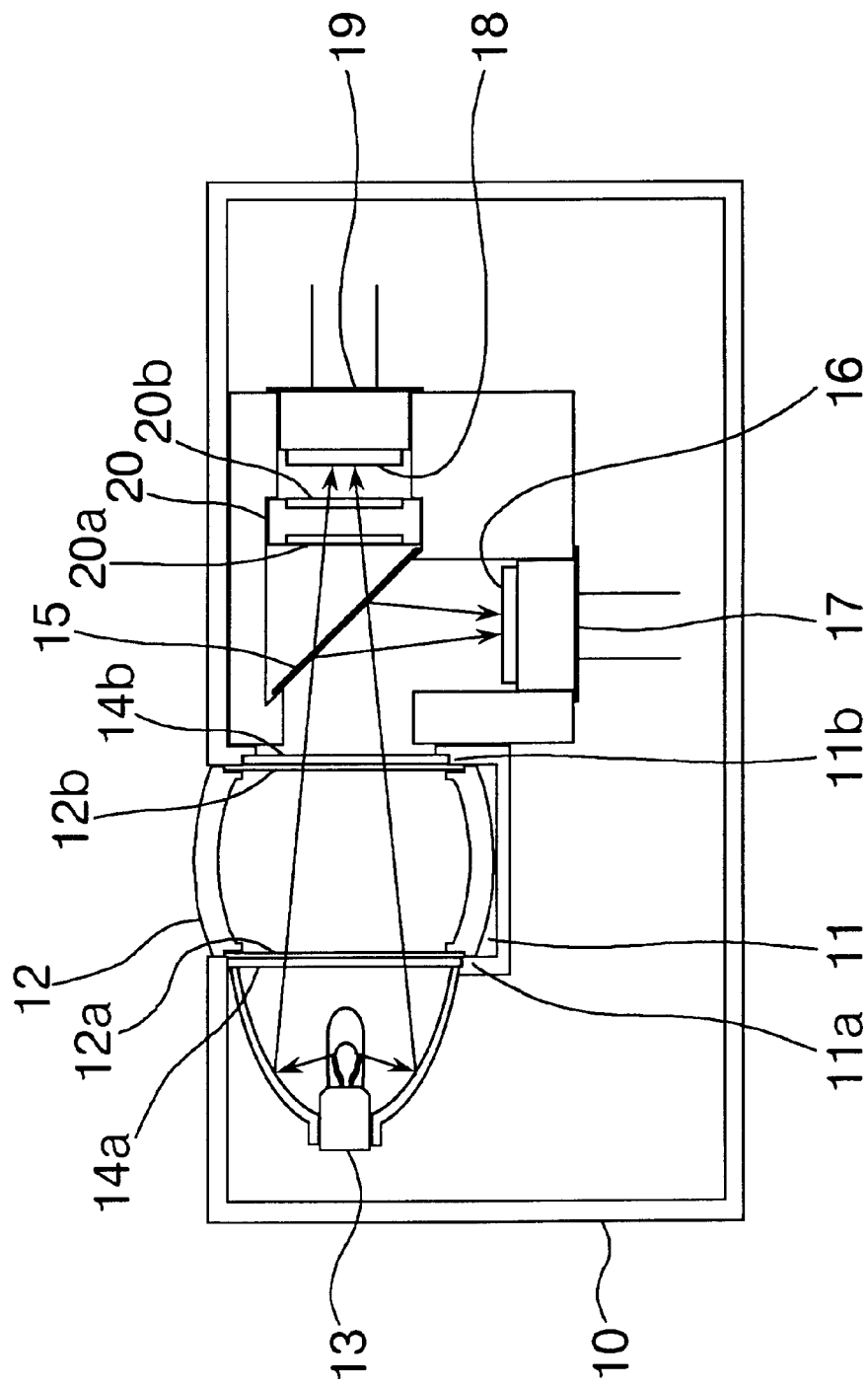
FIG. 1 is a sectional view showing a key portion of a capnometer which is an embodiment of the present invention.
Figure 3:
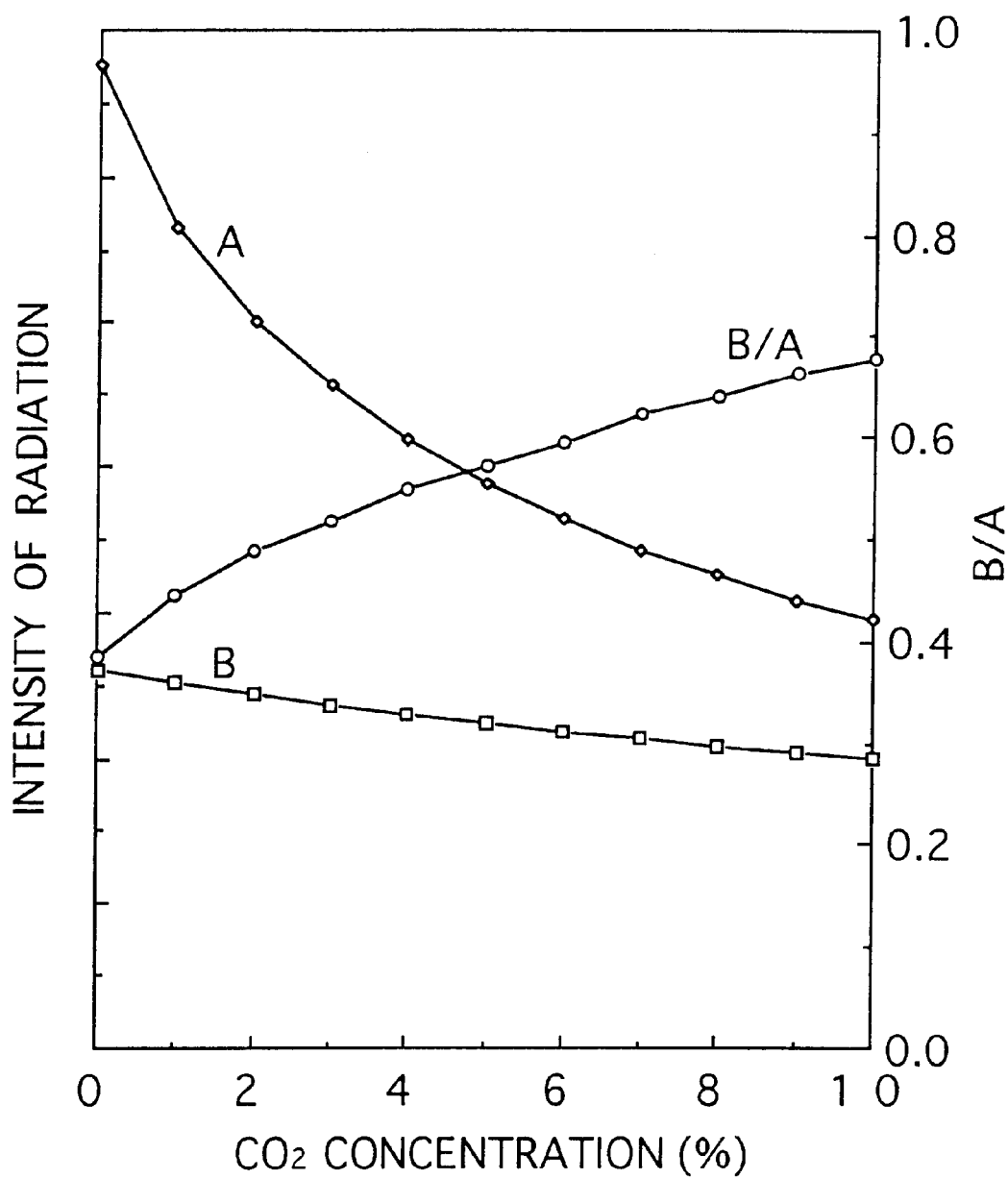
FIG. 3 is a graph showing variations of the output signals of the first and second detectors of the capnometer with respect to the concentration of carbon dioxide, and a ratio of the output signals.
Figure 4:
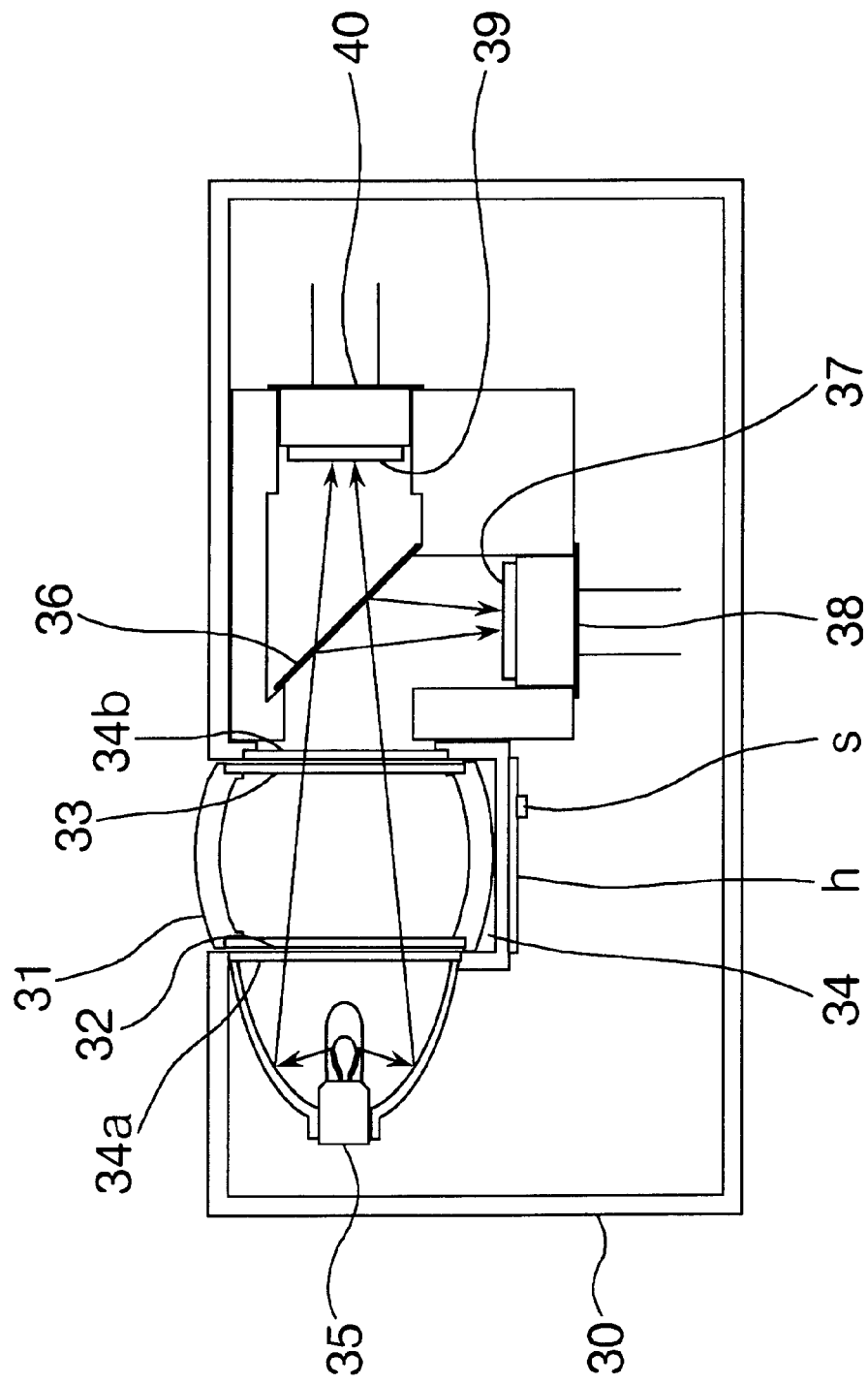
FIG. 4 is a sectional view showing a key portion of a conventional capnometer.

The preferred embodiment of an instrument (referred to as a capnometer) for measuring a concentration of carbon dioxide contained in respiratory gases will be described with reference to the accompanying drawings. FIG. 1 is a sectional view showing a major portion of a capnometer which is an embodiment of the present invention. FIG. 3 is a graph showing variations of the intensity of infrared radiation impinging on first and second detectors with respect to the concentration of carbon dioxide, and a ratio of the intensity of infrared radiation impinging on the first and second detectors as shown in FIG. 1.

An airway adaptor 12 is detachably inserted in a receptacle portion 11 of a housing 10 of an instrument (referred simply to as a capnometer) for measuring a concentration of carbon dioxide contained in a respiratory gas of a person. The airway adaptor 12, like the conventional one, is of the disposal type. An infrared radiation source 13 with a reflecting mirror is located on the left side of the receptacle portion 11. The airway adaptor 12 is inserted directly in the flow path between the ventilator and the endtracheal tube (not shown), which is extended in the directions vertical to the paper surface of the drawing.

Windows 12a and 12b are provided on both sides of the airway adaptor 12 when viewed in the direction of the optical axis of the infrared radiation source 13. A thin plastic film is used for forming the windows 12a and 12b of the airway adaptor 12 because it has a good transparency to the infrared radiation. If the windows 12a and 12b of the airway adaptor are not heated by a heater, water droplets deposit onto the inner surface of the windows and windows become fogged due to high humidity of respiratory gas. And scattering the infrared radiation by the droplets lower the transparency of the windows. To avoid fogging of the windows without heating the windows, the inner surface of the window is anti-fogging processed. A specific example of the film is a polyester film with anti-fogging coating. Not water droplets, but thin layer of the water is formed on the film surface because the film surface is hydrophilic. Infrared radiation is not scattered by thin water layer on the surface of the window, and fogging of the window is prevented. Therefore, there is no need of heating the windows in order to avoid fogging of the windows.

In the conventional art, as already described, the windows 12a and 12b of the airway adaptor 12 are made of expensive sapphire. Those expensive windows may be substituted by films with anti-fogging coating. As described above, there is no need of heating the windows in order to prevent the fogging of the windows. However, a thin layer of water is inevitably formed on the film surface. Sometimes, secretion of the patient, which contains mainly water, is deposit onto the inner surfaces of the windows 12a and 12b.

The detectors 40 and 38 generate electrical signals Is and Ir, which is propotional to the intensity of the incident infrared radiation. A ratio of those electrical signals is given by Is/Ir. As seen from an infrared transmittance spectrum of FIG. 5, the infrared transmittance of water ($H_2O$) varies with wavelength of light, viz., it is a function of wavelength $\lambda$. In a case where thin water layers are formed on 15 the inner surfaces of the windows 32 and 33 of the airway adaptor 31, the infrared transmittance is given by $T(\lambda)$. The output signals of the detectors 40 and 38 depend on $T(\lambda s) \cdot Is$ and $T(\lambda r) \cdot Ir$ where $\lambda s$ is the wavelength of light absorbed by the $CO_2$ gas, and $\lambda r$ is the wavelength of light not absorbed by the same. At this time, a ratio of the output signals of the detectors 40 and 38 is $T(\lambda s)/T(\lambda r) \cdot Is/Ir$. As seen from the infrared transmittance spectrum for water shown in FIG. 5, the infrared transmittance for water varies with the wavelength. With the transmittance variation, there is no case where the ratio of $T(\lambda s)/T(\lambda r)$ is 1. For this reason, it is impossible to use of the anti-fogging film for the airway adaptor 31 without heating in the conventional capnometer.

Openings 11a and 11b are provided also on both sides of the receptacle portion 11 when viewed in the direction of the optical axis of the infrared radiation source 13. Sapphire windows 14a and 14b are attached to the openings 11a and 11b of the receptacle portion, respectively.

A beam splitter 15 is slanted 45° with respect to the optical axis of the infrared radiation source 13. An infrared radiation impinges on the beam splitter 15, through the receptacle portion 11 and the airway adaptor 12. The beam splitter 15 allows part of the received infrared radiation in equal wavelength to transmit therethrough, but reflects the rest of the infrared radiation. For this reason, the beam splitter 15 may be formed with an inexpensive silicon plate, for example, while an expensive dichroic mirror for splitting the infrared radiation of different wavelengths is used in the prior capnometer.

After reflected by the beam splitter 15, the infrared radiation is impinging on a first detector 17 through a bandpass filter 16 of 4.3 μm in wavelength. The first detector 17, like the corresponding one in the prior analyzer, is a lead selenide detector, for example. The first detector 17 produces an electric signal, propotional to the intensity of the infrared radiation impinging on it. The present invention is not limited by this embodiment. The measurement could be performed to use a bandpass filter through which the infrared radiation within a range of 4.2 to 4.4 μm transmits.

After transmitting through the beam splitter 15, the infrared radiation impinges on a second detector 19 through a bandpass filter 18 of 4.3 μm in wavelength. The second detector 19 may have the same construction as of the first detector 17. The second detector 19 produces an electric signal, propotional to the intensity of the infrared radiation impinging on it.

In this embodiment of the invention, a gas cell 20 is disposed between the beam splitter 15 and the second detector 19. The gas cell 20 is filled with high concentration of $CO_2$ gas. Sapphire windows 20a and 20b are provided on both sides of the gas cell 20 when viewed in the direction of the optical axis of the infrared radiation impinging on the gas cell. The gas cell 20 absorbs the infrared radiation of 4.3 μm in wavelength, while allowing the infrared radiation of other wavelengths to transmit therethrough. In other words, the gas cell 20 has such a filtering function.

In the capnometer thus constructed, the infrared radiation is emitted from the infrared radiation source 13, and passes through the window 14a of the receptacle portion 11, the windows 12a and 12b of the airway adaptor 12, and the window 14b of the receptacle portion 11, and reaches the beam splitter 15. Part of the infrared radiation is reflected by the beam splitter 15 and impinges on the first detector 17 through the bandpass filter 16. The first detector 17 produces an electrical signal, propotional to the intensity of the infrared radiation impinging on it.

The rest of the infrared radiation transmits through the beam splitter 15, and reaches the second detector 19 by way of the gas cell 20 and the bandpass filter 18. The second detector 19 produces an electrical signal, propotional to the intensity of the infrared radiation impinging on it.

Variations of the output signals of the first and second detectors with respect to the concentration of carbon dioxide, and a ratio of the output signals of infrared radiations impinging on the first and second detectors, will be described with reference to FIG. 3. The output signal of the first detector 17 greatly decreases with an increase of the concentration of carbon dioxide within the airway adaptor 12 (as indicated by a curve A in FIG. 3). The output signal of the second detector 19 through the gas cell 20 slightly varies with a variation of the amount (concentration) of carbon dioxide within the airway adaptor 12 (as indicated by a curve B in FIG. 3). This is because the infrared radiation is greatly absorbed by the high concentration of the carbon dioxide within the gas cell 20.

A concentration of the carbon dioxide can be obtained by calculating a ratio (B/A) of the output signal A of the first detector 17 and the output signal B of the second detector 19, without any influence of a variation of the intensity of infrared radiation that is emitted from the infrared radiation source 13 the water layer, and soils of the windows 12a and 12b of the airway adaptor 12. Actually, a control unit (not shown) calculates the concentration of carbon dioxide by the utilization of the output signals of the first and second detectors 17 and 19.

In the embodiment under discussion, the infrared radiation of equal wavelength is detected by the first and second detectors 17 and 19. For this reason, the ratio of the intensity of the infrared radiation impinging on the first and second detectors is invariable even if the water layer is formed on the inner surfaces of the windows 12a and 12b of the airway adaptor 12. While the calculation error arises from the difference of the absorption amounts of the infrared radiation of 4.3 μm and 3.7 μm when the windows are soiled, and the light source suffers from the degradation and drift.

As described above, the wavelengths of the infrared radiations incident on the first and second detectors are equal to each other. The transmittance of a medium is a function of the wavelength of light transmitting through the medium, as described above. Therefore, the transmittance T is given by $T(\lambda)$ where $\lambda$ is the wavelength of light. An intensity of infrared radiation impinging on the first detector 17 is denoted as Is, and an intensity of infrared radiation impinging on the second detector 19 is denoted as Ir. Actual intensities of the infrared radiation impinging on the first and second detectors 17 and 19 are given by $T(\lambda s) \cdot Is$ and $T(\lambda s) \cdot Ir$ respectively. The ratio of the output signals of detectors are given by $$T(\lambda s) \cdot Ir / T(\lambda s) \cdot Is = Is / Ir$$

As seen from the above equation, the ratio of the output signals of the detectors is independent of $T(\lambda)$. This fact implies that even if a water layer is formed on the windows 12a and 12b in the airway adaptor 12 and the windows are soiled, the concentration of carbon dioxide can be measured independently of their transmittance values.

Since both the first and the second detectors detect the infrared radiation of approximately 4.3 μm in wavelength, the ratio (Is/Ir) of the output signals of the detectors 17 and 19 is invariable if the light source 13 suffers from its degradation and drift. Therefore, the concentration of the carbon dioxide may be measured free from the degradation and drift of the infrared radiation source.

Figure 2:
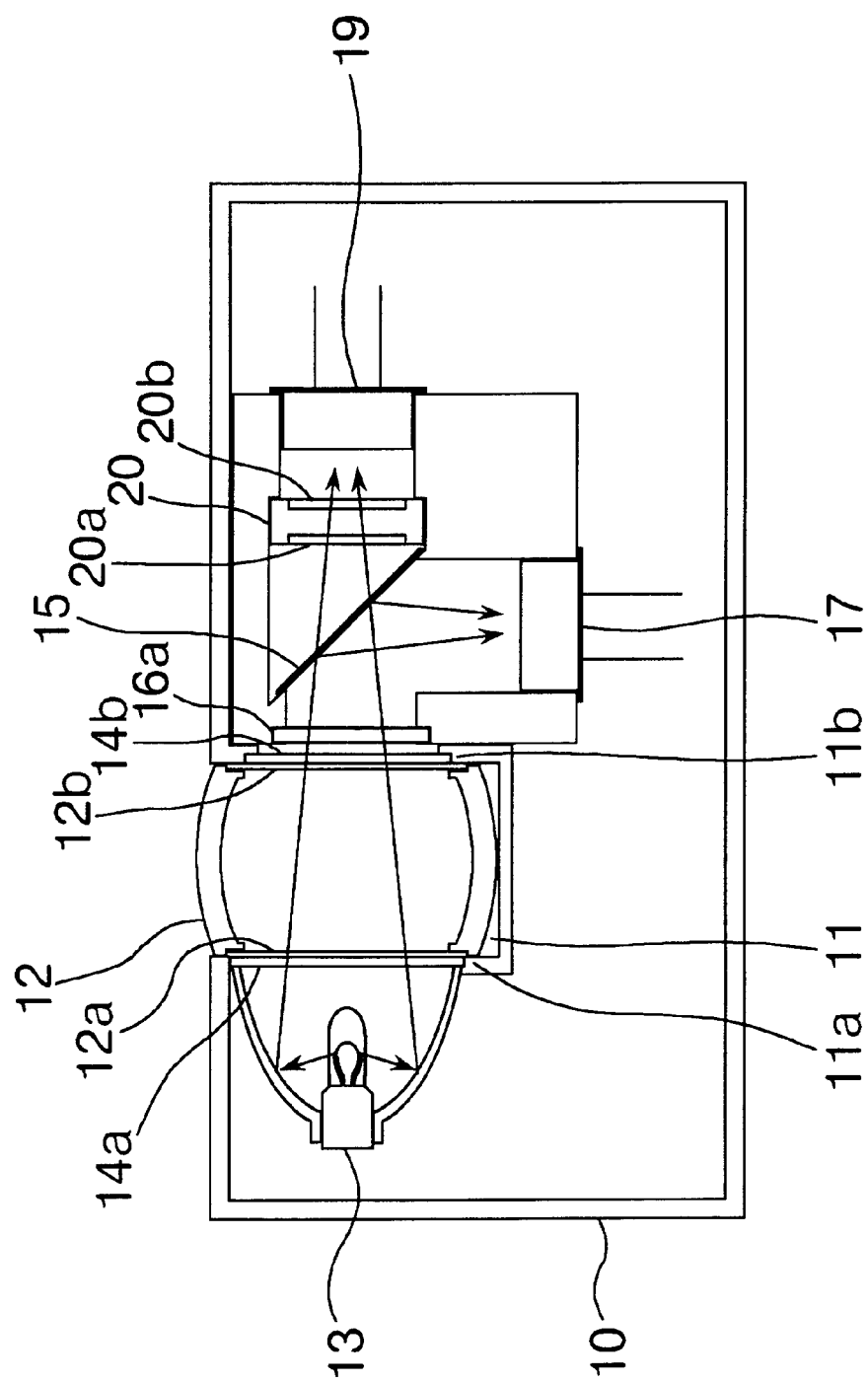
FIG. 2 is a sectional view showing a key portion of a capnometer which is another embodiment of the present invention.

In the embodiment mentioned above, the gas cell 20 is disposed between the beam splitter 15 and the second detector 19. If necessary, the gas cell 20 may be disposed between the beam splitter 15 and the first detector 17. Also in this case, it is possible to measure the concentration of carbon dioxide by use of the ratio of the output signals of the detectors 17 and 19, as a matter of course. The locations of the bandpass filters are not limited to those in the embodiment. For example, as shown in FIG. 2, a bandpass filter 16a may be disposed between the infrared radiation source 13 and the beam splitter 15. If so done, use of only one bandpass filter will do. This results in reduction of cost to manufacture. Usually, nitrogen is used for the gas filling the housing of the detector (19). $CO_2$ gas may be used in place of the $N_2$ gas. In this case, the detector may also be used as the gas cell. In other words, the detector and the gas cell are constructed as a unit. This leads to the size and cost reduction.

It should be understood that the invention is not limited in its application to the details of construction and arrangement of parts illustrated in the accompanying drawings.

As mentioned above, in the capnometer of the present invention, the detectors detect infrared radiation having an equal wavelength. Therefore, the analyzer can exactly measure the concentration of carbon dioxide independently of the water layer formed on the inner surfaces of the windows in the airway adaptor, soils of the windows, and the degradation and drift of the infrared radiation source.

In the embodiment of the invention, there is no need for the heater and thermistor, which are indispensable for preventing the windows of the airway adaptor from being fogged in the conventional capnometer. This feature contributes to reduction of power consumption by the analyzer and simplification of the analyzer construction.

Further, there is no need for expensive material, such as sapphire, for the windows of the airway adaptor. Besides, such a simple and inexpensive beam splitter as to be able to reflect the infrared radiation and allow the same to pass therethrough is available for the capnometer of the embodiment of the invention, while an expensive dichroic mirror capable of splitting two infrared radiation of different wavelengths is used for the conventional analyzer.

What is claimed is:

1. A carbon dioxide gas analyzer for determining a concentration of a carbon dioxide gas in a respiratory gas of a subject, comprising:

a detachable airway adaptor for introducing a respiratory gas into the analyzer, and comprising a plurality of windows through which light passes, said plurality of windows having an anti-fogging characteristic;

an infrared light source for emitting infrared radiation which passes through said airway adaptor;

a beam splitter for reflecting and transmitting infrared radiation impinging thereon, after the infrared radiation has passed through said airway adaptor;

first detecting means for detecting the infrared radiation reflected by said beam splitter;

second detecting means for detecting the infrared radiation transmitted through said beam splitter;

a gas cell filled with a gas including carbon dioxide, and located between said beam splitter and one of said first and said second detecting means;

two bandpass filters for allowing only an infrared radiation having wavelength of approximately 4.3 $\mu$m to transmit through, said bandpass filters being respectively located between said first detecting means and said beam splitter and between said second detecting means and said beam splitter, such that said first and said second detecting means detect only an infrared radiation having wavelength of approximately 4.3 $\mu$m; and processing means for processing a concentration of carbon dioxide gas in a respiratory gas based on a ratio of output signals from said first and said second detecting means;

wherein said respective infrared radiation detected by said first and said second detecting means is from infrared radiation that has passed through said airway adaptor along only a single beam passageway.

2. The carbon dioxide gas analyzer according to claim 1, wherein said ratio is invariable when a water layer is formed on said windows.

3. The carbon dioxide gas analyzer according to claim 1, wherein said beam splitter is made of a silicon plate.

4. A carbon dioxide gas analyzer for determining a concentration of a carbon dioxide gas in a respiratory gas of a subject, comprising:

a detachable airway adaptor for introducing a respiratory gas into the analyzer, and comprising a plurality of windows through which light passes, said plurality of windows having an anti-fogging characteristic;

an infrared light source for emitting infrared radiation which passes through said airway adaptor;

a beam splitter for reflecting and transmitting infrared radiation impinging thereon, after the infrared radiation has passed through said airway adaptor;

first detecting means for detecting the infrared radiation reflected by said beam splitter;

second detecting means for detecting the infrared radiation transmitted through said beam splitter;

a gas cell filled with a gas including carbon dioxide, and located between said beam splitter and one of said first and said second detecting means;

a bandpass filter for allowing only an infrared radiation having wavelength of approximately 4.3 $\mu$m to transmit therethrough, said bandpass filters being respectively located between said airway adaptor and said beam splitter, such that said first and said second detecting means detect only an infrared radiation having wavelength of approximately 4.3 $\mu$m; and processing means for processing a concentration of carbon dioxide gas in a respiratory gas based on a ratio of output signals from said first and said second detecting means;

wherein said respective infrared radiation detected by said first and said second detecting means is from infrared radiation that has passed through said airway adaptor along only a single beam passageway.

5. The carbon dioxide gas analyzer according to claim 4, wherein said ratio is invariable when a water layer is formed on said windows.

6. The carbon dioxide gas analyzer according to claim 4, wherein said beam splitter is made of a silicon plate.

* * * * *